(12) United States Patent
Sekine et al.

(10) Patent No.: US 6,692,958 B2
(45) Date of Patent: Feb. 17, 2004

(54) CORD BLOOD-DERIVED ACTIVATED LYMPHOCYTES, PREPARATIONS CONTAINING SAID LYMPHOCYTES AS MAIN INGREDIENT AND METHOD AND KIT FOR PRODUCING SAID PREPARATIONS

(75) Inventors: Teruaki Sekine, Tokyo (JP); Kiminari Ito, Hokkaido (JP); Norio Shimizu, Yamanashi (JP); Kenzo Bamba, Ibaraki (JP); Tomohiro Yamaguchi, Saitama (JP); Yasuyuki Kuroiwa, Ibaragi (JP)

(73) Assignee: Humantec Ltd., Ibaraki-ken (JP)

( * ) Notice: Subject to any disclaimer, the term of this patent is extended or adjusted under 35 U.S.C. 154(b) by 19 days.

(21) Appl. No.: 10/003,539

(22) Filed: Dec. 4, 2001

(65) Prior Publication Data

US 2002/0086063 A1 Jul. 4, 2002

(30) Foreign Application Priority Data

Dec. 4, 2000 (JP) ......................................... 2000-368287

(51) Int. Cl.$^7$ ............................ C12N 5/08; C12N 5/00; C07K 1/00; A61K 38/21; A01N 63/00
(52) U.S. Cl. ....................... 435/372; 435/386; 530/351; 424/85.4; 424/93.71
(58) Field of Search ................................ 435/372, 386; 530/351; 424/85.4, 93.71

(56) References Cited

U.S. PATENT DOCUMENTS 5,928,639 A * 7/1999 Slavin ..................... 424/93.71

OTHER PUBLICATIONS

E. Walter et al., "Reconstitution of Cellular Immunity Against Cytomegalovirus in Recipients of Allogeneic Bone Marrow by Transfer of T–Cell Clones from the Doner", The New England Journal of Medicine, vol. 333:1038–1044, No. 16, Oct. 19, 1995, pp. 1–26.

C. Emmanuel et al., "Characterization of T Cell Repertoire in Patients with Graft–Versus–Leukemia after Donor Lymphocyte Infusion", J. Clin. Invest., vol. 100, No. 4, Aug. 1997, pp. 855–866.

H. Kolb et al., "Graft–Versus–Leukemia Effect of Donor Lymphocyte Transfusions in Marrow Grafted Patients", Blood, vol. 86, No. 5, Sep. 1, 1995, pp. 2041–2050.

S. Giralt et al., "CD8–Depleted Donor Lymphocyte Infusion as Treatment for Relapsed Chronic Myelogenous Leukemia after Allogeneic Bone Marrow Transplantation", Blood, vol. 86, No. 11, Dec. 1, 1995, pp. 4337–4343.

S. Slavin et al., "Allogeneic Cell Therapy for Relapsed Leukemia after Bone Marrow Transplantation with Donor Peripheral Blood Lymphocytes", Experimental Hematology, vol. 23, 1995, pp. 1553–1562.

Kamiya Ito and Teruaki Sekine, Monthly Magazine, "Igakunoyumi" Ishiyaki Pub. Inc., vol. 181, No. 6, May 10, 1997, pp. 426–427 (In Japanese).

* cited by examiner

*Primary Examiner*—Hankyel T. Park
(74) *Attorney, Agent, or Firm*—Wenderoth, Lind & Ponack, L.L.P.

(57) ABSTRACT

Activated lymphocytes derived from cord blood are excellently effective for preventing and treating various types of tumors and various types of infection. With interleukin 2 and/or anti-CD3 antibody, the lymphocytes derived from the cord blood is prepared by segregating lymphocytes from the cord blood and proliferating the segregated lymphocytes directly in vitro or segregating monocytes from cord blood and proliferating the monocytes in vitro. Also, the cord blood-derived activated lymphocytes can be effectively used for preventing recurrence of the diseases and promoting the take of stem cells or other organs.

23 Claims, No Drawings

CORD BLOOD-DERIVED ACTIVATED LYMPHOCYTES, PREPARATIONS CONTAINING SAID LYMPHOCYTES AS MAIN INGREDIENT AND METHOD AND KIT FOR PRODUCING SAID PREPARATIONS

BACKGROUND OF THE INVENTION

1. Field of the Invention

This invention relates to activated lymphocytes derived from cord blood, pharmaceutical preparations containing the aforesaid activated lymphocytes as a main ingredient, and a method and kit for producing the aforesaid preparations for the purpose of treating various tumors and infection diseases and preventing these diseases from developing and redeveloping and hastening take of stem cells of various organs and so on.

2. Description of the Prior Art

Lately, intense interest has been shown toward lymphocytes bearing an immune system for biophylaxis. Specifically, T-lymphocytes are one of the important cells having an efficient cellular immunity and sorted into the following groups in accordance with the reactivity of monoclonal antibodies. For example, the T-lymphocytes having reactivity with anti-CD3 antibodies ("CD" is short for "cluster of differentiation) belong to CD3 positive cells. There have been performed a number of studies of the relationship between the antigen manifested from these lymphocytes and their functions.

The lymphocyte manifesting CD45 RA-antigen among the CD3 positive cells is a naive T-lymphocyte, which is deemed not to have antitumor activity. On the contrary, the lymphocyte manifesting CD45 RO-antigen among the aforesaid CD3 positive cells is a memory T-lymphocyte, which is recognized to have the function of antitumor activity. Sekine, one of the inventors, has already reported that it is possible to proliferate the lymphocytes with a solidus anti-CD3 antibody and interleukin 2, so that autologous lymphocytes obtained as the result of proliferation can possess an antitumor function (Japanese Patent Public Disclosure HEI 03-80076(A)).

There have been made any reports that the lymphocytes derived from peripheral blood or the like can be proliferated by using the anti-CD3 antibody or interleukin 2, thus to produce autologous lymphocytes having an antitumor function. Further, Ito et al., some of the inventors of this invention, have reported that the autologous lymphocytes proliferated with the anti-CD3 antibody and interleukin 2 is effective against viral infections of a patient of innate immunodeficiency (Kimiya Ito and Teruaki Sekine, Monthly Magazine "Igakunoayumi" Ishiyaku Pub. Inc., Vol. 181 (1997), No. 6, pp. 426–427).

Bone marrow transplant is generally performed in a case that a patient and a donor are compatible with each other in leukocyte blood group (hereinafter abbreviated as "HLA"). However, since there are many types of HLA, it is remarkably rare that the HLAs of the patient and donor are identical with each other. With the existing state of affairs, the bone marrow transplant has been performed when only the chief components of the HLA are identical between the patient and donor. Disadvantageously, incomplete match of the HLA between the patient and donor possibly cause host diseases (hereinafter abbreviated as "GVHD") in the bone marrow transplant.

For the purpose of treating the GVHD disease, which brings about a serious case, an immune inhibitor is used. The patient dosed with the immune inhibitor gets over the disease for the time being, but mostly gets into a serious situation of developing cytomegalovirus or Epstein-Barr virus infections, resulting in death. Thus, Elizabeth et al. reported that the cytomegalovirus infections of the patient of bone marrow transplant can be treated by inducing specific CD4 positive cells from the lymphocytes of the bone marrow donor, thereby to prevent and treat the virus infections caused in the immunosuppressive conditions (Elizabeth A. Walter, M.D. et al., The New England Journal of Medicine, Vol.333, pp.1038–1044).

Furthermore, allogenic lymphocytes prepared by a pheresis procedure have been clinically used for treating a leukemia patient, i.e. donor leukocyte transfusion (hereinafter abbreviated as "DLT"). Although DLT has a high therapeutic value, it was confirmed that the treatment using DLT caused 50% to 80% of the leukemia patients to suffer from acute GVHD and some 20% of the leukemia patients to suffer from lathal GVHD (Kolb. H. J. et al. Blood, Vol.86, pp.2041–2050 (1995), and Slavin S. et al., Experimental Hematology, Vol.23, pp.1553–1562 (1995)). It takes a long time to perform the pheresis, thus to impose an oppressive burden on the donor.

Giralt et al. reported about DLT using leukocyte free from CD8 positive cells (Giralt, S. et al., Blood, Vol.86, pp.4338–4343 (1995)). Ritz et al. reported about DLT using CD4 positive cells prepared by pheresis (Claret E J. et al., Journal of Clinical Investigation, Vol.100, No.4, pp.855–866 (1997)). It was reported that, in either case, the effect of GVL (abbreviated from "Graft versus leukemia"), in which slight GVL favorably affects a patient, is created, but the GVL effect is weak.

Recently, there has been studied an attempt to use cells contained in cord blood instead of the cells prepared from peripheral blood or marrow blood, which has been practically superseded by a marrow-bone transplant. However, in general, the lymphocyte contained in the cord blood is a naive lymphocyte, which is not irritated by antigens, and thus, is usually deemed not to possess antitumor activity nor an antiviral effect.

The cord blood contained in an umbilical cord can be obtained without imparting a burden on the donor and is little in restriction on HLA. Therefore, it is advantageous to the donor in comparison with collection of cells from the bone marrow or peripheral blood. However, cord blood inoculation may possibly redevelop a tumor with greater frequency and is disadvantageous from the standpoint of the possibility of viral infections and the take of the cells inoculated.

OBJECT OF THE INVENTION

An object of the present invention is to provide activated lymphocytes and pharmaceutical preparations containing the activated lymphocytes, which can be inoculated onto a receptor with secure against redevelopment of a tumor, eliminating the possibility of causing viral infections and recurring a tumor caused by cord blood transplant.

Another object of the present invention is to provide activated lymphocytes and pharmaceutical preparations prepared from activated lymphocytes, which has high ability of take of cells in the preparations inoculated.

Still another object of the present invention is to provide a method and kit, which can produce pharmaceutical preparations capable of being inoculated onto a receptor with secure against redevelopment of a tumor, eliminating the possibility of causing viral infections and recurring a tumor caused by cord blood transplant

SUMMARY OF THE INVENTION

To attain the objects described above according to the present invention, there is provided activated lymphocytes, which are derived from cord blood and proliferated. The lymphocytes derived from the cord blood is prepared by segregating lymphocytes from the cord blood and proliferating the segregated lymphocytes directly in vitro or segregating monocytes from cord blood and proliferating the monocytes in vitro. The segregated lymphocytes or monocytes are activated and proliferated with interleukin 2 and/or anti-CD3 antibody.

The lymphocytes derived from the cord blood according to the invention can be inoculated onto a receptor or a patient with secure against redevelopment of a tumor, eliminating the possibility of causing virus-infected diseases, i.e. viral infections, and recurring a tumor caused by cord blood transplant.

Pharmaceutical preparations according to the present invention are prepared by segregating monocytes from cord blood, activating and proliferating the monocytes thus segregated with interleukin 2 and/or anti-CD3 antibody to obtain activated and proliferated lymphocytes, and adding the activated and proliferated lymphocytes thereto as a main ingredient.

The pharmaceutical preparations according to the invention serves to treat a tumor and infection diseases and prevent these diseases from developing and redeveloping.

Further, the present invention provides a method and kit for producing activated lymphocytes derived from cord blood, comprising the processes of segregating monocytes from cord blood, and activating and proliferating the monocytes thus segregated with interleukin 2 and/or anti-CD3 antibody to obtain activated and proliferated lymphocytes.

According to the method and kit of the present invention, the desired high-ability activated lymphocytes and pharmaceutical preparations, which can be inoculated onto a receptor with secure against redevelopment of a tumor, eliminating the possibility of causing viral infections and recurring a tumor caused by cord blood transplant, can be obtained.

Other and further objects of this invention will become obvious upon an understanding of the embodiments described hereinafter or will be indicated in the appended claims, and various advantages not referred to herein will occur to one skilled in the art upon employment of the invention in practice.

DESCRIPTION OF THE PREFERRED EMBODIMENTS

The method for producing activated lymphocytes derived from cord blood, pharmaceutical preparations containing the activated lymphocytes as a main ingredient according to the present invention will be described in detail hereinbelow.

[Cord Blood Collecting]

The activated lymphocytes derived from cord blood in the present invention can be obtained by activating and proliferating the cord blood gathered from an umbilical cord. It is desirable to draw the cord blood from a blood vessel of the umbilical cord. Further, heparin or citric acid may be added to the cord blood gathered so as to prevent the gathered cord blood from coagulating. A part of cord blood preserved for transplantation at a cord blood bank may be used. The activated lymphocytes derived from the cord blood according to the invention can be prepared from 0.001 ml to 100 ml of cord blood.

[Cord Blood-derived Activated Lymphocytes]

Proliferation of the activated lymphocytes derived from the cord blood is accomplished by a commonly known cultivating method for lymphocytes. The present invention does not specifically contemplate imposing any limitation on the cultivating method. For example, the activated lymphocytes of the invention may be proliferated in the presence of either or both of interleukin 2 and anti-CD3 antibody. From the viewpoint of the efficiency of proliferation, it is desirable to perform the proliferation in the presence of both the interleukin 2 and anti-CD3 antibody.

In the case of the proliferation in this embodiment of the invention, the interleukin 2 on the market may be used. It is preferable to use a culture medium for cultivating the lymphocytes so as to have a concentration of 1000 to 2000 U/ml of the activated lymphocytes thus obtained. In use, the interleukin 2 in this embodiment may be dissolved in a common culture medium for cultivating cells. That is, the method according to the invention may adopt the culture medium such as water, physiological saline, Dulbecco's phosphate buffered saline solution, RPMI-1640, DMEM, IMDM and AIM-V, which are widely used in this field. It is desirable to cryopreserve the interleukin 2 once dissolved in order to prevent decrease of the activity thereof.

The type of such a culture medium is not specifically limited in the present invention, and any type of culture medium congenial to the lymphocyte cell to be cultivated may be used in the invention. For example, there may be used a synthetic medium obtained by adding amino acids, vitamins and/or nucleic acid bases to a culture fluid derived biologically from serum and so on or equilibrium saline solution. RPMI-1640, AIM-V, DMEM, IMDM or the like may be used as the culture medium. Of these mediums, RPMI-1640 is desirably used. Specifically, a normal human serum has an excellent proliferating effect, and therefore, may suitably be used as the culture medium for cultivation of the lymphocytes. These culture mediums noted herein are available on the market.

The cultivation of the lymphocytes can be fulfilled, for example, in an incubator by a common cell cultivating method. It is suitable to perform the cultivation at a concentration of 1 to 10%, preferably 5%, of carbon dioxide at 30° C. to 40° C., preferably 37° C. The number of days required for cultivation is not limited in the invention, but it is desirable to caltivate the lymphocytes for 2 to 20 days, more preferably 3 to 14 days, so that stimulus information of the anti-CD3 antibodies is transmitted to the cells. It is desirable to add an appropriate amount of culture solution to the culture medium while the state of the cells is observed under a microscope to count the number of the cells in the course of the cultivation.

The cells under the cultivation do not markedly change in a few days after the commencement of the cultivation, but generally begin to proliferate after the lapse of three days. During the period, satisfactory cultivation causes the culture solution to change orange color to yellow color. It is advisable to add the culture solution to the culture medium every one to seven days in order to prevent deterioration of the culture solution and a lowering of the interleukin 2.

After completion of the cultivation in the presence of the anti-CD3 antibodies, the cultivation may be further continued in the absence of anti-CD3 antibody. That is, the lymphocytes may be continuously cultivated in a vessel having no anti-CD3 antibody contained therein, such as a cultivating flask, roller bottle and cultivating gas-permeable bag. The cultivation may be continued until the lymphocytes are administered to a patient. Although the cultivation of the lymphocytes are performed under the conditions noted here, it is advisable to perform the cultivation of the lymphocytes under the same conditions as that in the presence of anti-CD3 antibodies as described above. That is, use of the human serum having an appropriate concentration and a serum-free culture medium in the cultivation of the lymphocytes proves very advantageous from standpoint of cost, workability and safety.

In starting the cultivation of the lymphocytes, for example, cord blood or monocytes may be suspended in the culture solution containing interleukin 2 and placed in a culture vessel having the anti-CD3 antibody in a solid phase. Further, there may be used various types of cytokines, proliferation activating factors, mitogens or the like for proliferating and activating the cord blood-derived lymphocytes.

The anti-CD3 antibody for stimulating the lymphocyte cells may be yielded in a plant or an animal by using purified CD3 molecules, and it is convenient to use commercial OKT-3 antibodies (produced by Ortho Pharmaceutical Corp.) having advantages in stability and cost. However, this invention does not contemplate imposing any limitation on the antibody, and can adopt any other antibodies capable of promoting proliferation and activation of the lymphocyte cells.

It is desirable to use solid-phase anti-CD3 antibody from the viewpoint of the proliferating efficiency and handling properties of the lymphocyte cells. An implement for making the antibody into a solid phase, a proliferating vessel made of glass, polyurethane, polyolefine, polystyrene or the like may be used. Also, a sterilized plastic flask for proliferating cells may be used. A suitable size of the proliferating vessel may be selected.

The solidification for making the anti-CD3 antibody into a solid phase is performed by adding the diluted solution of the anti-CD3 antibody into a specified implement and allowing it to stand at a temperature of, for example, 4 to 37° C. for 2 to 24 hours. In the embodiment of the present invention, it is desirable to use the solid anti-CD3 antibody diluted with physiologic Dulbecco's phosphate buffered saline solution to a concentration of 0.1 to 30 $\mu$g/ml. After solidifying, the solid anti-CD3 antibody thus obtained is preserved in a cold room or freezer (4° C.) until use. In use, the solution is removed. If necessary, the anti-CD3 antibody may be rinsed with Dulbecco's phosphate buffered saline solution or the like at room temperature.

The cord blood-derived lymphocytes thus obtained is further processed to preparations described later. The preparations produced from the cord blood-derived lymphocytes are effectively used widely in treating, preventing or alleviating various diseases such as tumor and infections.

The term "preparations" used herein means all the substances having a biophylactic function, which contain the cord blood-derived lymphocytes as a main ingredient. Namely, any preparations containing the cord blood-derived lymphocytes may be used. For instance, the cord blood-derived lymphocytes suspended in an appropriate solution may be used. Although the form in which the cord blood-derived lymphocytes are suspended in a physiological saline for fluid therapy, which contains human serum albumin, may be desirably used, this is not specifically limited in the invention.

In the embodiment of the invention, the preparations containing the cord blood-derived lymphocytes as a main ingredient as noted above can be produced by proliferating cord blood directly in a test tube, or segregating monocytes from cord blood, and activating and proliferating the monocytes thus segregated with interleukin 2 and/or anti-CD3 antibody.

The cord blood-derived lymphocytes in the preparations according to the present invention may be prepared with various genes or default or modified ones of intrinsic genes. By using the cord blood-derived lymphocytes lacking the necessary cofactors for infection of human immunodeficiency virus, it is possible to prevent and treat the infection of human immunodeficiency virus or various infections caused in an immunological deficiency condition by the human immunodeficiency virus. Furthermore, although it is a matte of course that the preparations according to the present invention can be used in the case that the donor and patient match each other in HLA, the preparations of the invention can be used even when the donor and patient do not match in HLA.

The preparations containing, as a main ingredient, the cord blood-derived lymphocytes according to the invention can be applied treating and preventing diseases of cancers, immunodeficiency, autoimmune diseases, a patient of allergic disease to be subjected to cord blood stem cell transplantation, and various infections diseases.

The preparations according to the invention can be effectively used for treating and preventing not only various tumors as noted above, but also leukemia and other solid carcinoma.

As the cancers which can be treated with the preparations of the invention, there are enumerated lung cancer, stomach cancer, colon cancer, rectal cancer, liver cancer, pancreas cancer, gallbladder cancer, ovarian cancer, uterine cancer, testis cancer, prostate cancer, leukemia, sarcoma, brain tumor, etc. The immunological deficiency syndromes are grouped into acquired immunodeficiency and inborn immunodeficiency. The acquired immunodeficiency against which the preparations according to the invention are effective includes severe combined immunodeficiency (SCID), Wiscott Aldric syndrome, adenosine deaminase coloboma, and purine nucleoside phosphorylase coloboma. However, the present invention does not contemplate imposing any limitation only on these syndromes.

The inborn immunodeficiency against which the preparations according to the invention are effective includes secondary immunodeficiency caused by use of carcinostatic preparation, immunosuppressive preparation or steroid, AIDS caused by human immunodeficiency viral infections. However, the present invention does not contemplate imposing any limitation only on these diseases. The autoimmune diseases against which the preparations according to the invention are effective include systemic lupus erythematosus, chronic rheumatism, Sjogren syndrome, myasthenia gravis, pernicious anemia, and Hashimoto's disease, but the present invention does not contemplate imposing any limitation only on these diseases.

Further, the preparations according to the present invention can be provided for not only a patient having reduced immunity, a patient having no immunity to a specific virus in treating and preventing. The allergic diseases against which the preparations according to the invention are effective include bronchial asthma, Japanese cedar pollinosis, cnidosis, nettle rash, etc. However, the present invention does not contemplate imposing any limitation only on these diseases. The preparations according to the present invention can be used for treating, preventing and alleviating various types of allergic diseases.

The infections against which the preparations according to the invention are effective include viral infections, microbism infections, mycete infections, protozoan infections, Chlamydia infections, mycoplasma infections, etc. Of the viral infections, there are infections caused by cytomegalovirus, and Epstein-Barr virus. However, the present invention does not contemplate imposing any limitation only on these infections. That is, the preparations according to the present invention are effective in treating and preventing various viral infections caused by herpesviruses such as herpes simplex virus and Variccela-zoster virus, and retro viruses such as human leukemia virus, and human immunodeficiency virus.

The aforesaid microbism infections against which the preparations according to the invention are effective include those caused by pyocyanolysin, Methicillin Resistant Staphylococcus aureus (MRSA) and other pathogenic bacilli. The preparations according to the invention can be used even for infections caused by pathogens which are unknown or hard to identify, and their incidental diseases.

[Kit for Producing Preparations Containing the Cord Blood-derived Activated Lymphocytes as a Main Ingredient]

Although the components of the activated lymphocytes derived from cord blood according to the present invention can be independently used as a reagent, a combination of the cord blood-derived lymphocytes, culture solution and flask for solidifying the anti-CD3 antibody constitutes a kit for producing the cord blood-derived activated lymphocytes according to the invention. With this kit, the preparation according to the invention can be ensurely prepared with ease.

The culture solution used in the kit of the invention may be placed into the flask for solidifying the anti-CD3 antibody in advance. The cord blood-derived activated lymphocytes stored in the flask may be cryopreserved. Thus, by preparing the kit composed of at least two components as a plurality of reagents, the preparations according to the present invention can easily be produced and placed at the service of preventing and treating various viral infections and various diseases as noted above.

The preparations containing the cord blood-derived activated lymphocytes according to the invention may be preserved in the frozen state and used for preventing and treating various diseases as required.

[Dosage]

The amount of the preparations containing the aforesaid activated lymphocytes as a main ingredient, which are produced by the method of the present invention, may be arbitrarily determined in accordance with the conditions and state of a patient to be dosed with the preparations of the invention. In general, the lymphocytes on the order of $1 \times 10^3$ to $1 \times 10^8$ may be suitably administered per 1 kilogram of patient's weight. Preferably, the lymphocytes in the range of $1 \times 10^3$ to $1 \times 10^8$ may be administered to the patient in expectation of the efficiency of the preparations.

[Administration]

It is desirable to administer, to the patient, the preparations according to the present invention in the form of an injection or an intravenous drip. It is more preferable to use the injection or intravenous drip containing a physiological saline to which the aforesaid cells is added so as to have a concentration of 0.01% to 5% of human serum albumin. The administration of the preparations according to the invention may be suitably performed by an intravenous drip or an injection into a vein, artery or local. Although the amount of the preparations to be administered depends on the administering method or region, it is desirable to administer 1 to 500 ml of the preparations. It is more desirable to use the desirable amount of preparations containing the prescribed amount of cells described above. It is recommended that the frequency with which the preparations of the invention are administered to the patient is one per day to one per month, and the number of the administration of the preparations is at least one.

Experimental Embodiment 1

1. Arrangement of Cultivating Flask:

3 ml of OKT3 solution (produced by Ortho Pharmaceutical Corp. and imported by Janssen-Kyowa Co., Ltd.) diluted to 5 $\mu$g/ml with Dulbecco's phosphate buffered saline solution (sold by Nipro Medical Corporation) was transfused into a cultivating flask (MS-200 made by Sumitomo Bakelite Company Ltd.) so as to soak the bottom of the flask in the solution.

The solution contained in the cultivating flask was preserved in a freezer overnight, and thereafter, OKT3 was sucked out by an evacuator. Then, Upon pouring 10 ml of physiological saline into the flask, the flask kept covered was vehemently shaken, and then, opened to take out the solution. Further, 01 ml of physiological saline solution (Hikari Pharmaceutical Co. Ltd.) was added into the flask. Upon covering the flask with the lid, the flask was vehemently shaken. Thereafter, the flask was opened and remaining liquid contents were courteously removed from the flask and lid.

In the flask, a mixture of 43.5 ml of culture medium (RPMI1640+7 made by Nikken Bio Medical Laboratory Inc.) and 35,000 U/ml of IL-2 (made by Cetus Corporation), 0.5 ml of Fungizone (imported and sold by Life Technologies Oriental Inc.), and 0.5 ml of human serum were mixed to obtain a culture medium. The same three flasks were prepared. The flasks were preserved in a freezer just before use.

2. Blood-collecting:

There were collected 5 to 20 ml of cord blood from umbilical cords of three donors with addition of heparin.

3. Cultivation of Cord Blood Collected:

At the outset, the flasks prepared in the process 1 noted above were taken out of the freezer and allowed to stand for 10 minutes. Upon confirming that the culture medium was completely dissolved in each flask, the cord blood obtained in the process 2 noted above was poured by 100 $\mu$l into each of the three flasks and lightly stirred so as to uniformly disperse the cord blood in each flask. Thereafter, cultivation was started in an incubator (MIP-3033 made by Sanyo Electric Biomedical Co., Ltd.) at a humidity of 95% at a concentration of 5% $CO_2$ (first day).

4. Measurement of the Number of Cells by Using Turk's Solution:

10 $\mu$l of cord blood collected in the process 2 above was mixed with 40 $\mu$l of Turk's solution (made by Muto Kagaku Yakuhin). The mixture was applied by 10 $\mu$l to a hemocytometer (Product No. 9731 made by Perkin-Elmer Corporation), and measured to count the number of cells under a microscope (Model 211320 made by Olympus Optical Co., Ltd.) There was obtained the result that the total numbers of the cells in the three flasks were $1.3 \times 10^5$, $1.5 \times 10^5$ and $1.4 \times 10^5$, respectively.

5. Segregation of Cord Blood Monocytes for Analysis of Cell-Surface Antigens:

A hypodermic needle was aseptically taken off from a syringe containing the cord blood thus collected in a clean bench (Model S-1100 made by Showa Science Co., Ltd.) without touching the joint portion between the syringe and needle and replaced with another hypoderic needle (19G× 1·½" needle made by Nipro Medical Corporation). Then, 5 ml of rinsing culture medium (made by Nikken Bio Medical Laboratory Inc.) was put into a centrifugal settler tube for volume 15 ml (Product No. 2327-015 made by Iwaki Glass Co., Ltd.), and further, the blood collected was slowly added into the centrifugal settler tube. Thereafter, the centrifugal settler tube was tightly covered with a lid, and then, turned upside down several times to mingle.

Next, into the centrifugal settler tube of 15 ml in volume, there were 15 ml of Lymphosepar-1 (made by Immuno-Biological Laboratories Co., Ltd.) was transfused by using a pipet of 10 ml in capacity (Pipet 4105 imported and sold by Corning International). Then, 10 ml of cord blood diluted with the rinsing culture medium were poured into the centrifugal settler tube, and thereafter, centrifuged at a relatively low speed of 1800 rpm at a centrifugal separating temperature of 20° C. for 15 minutes with a centrifugal separator with its brakes off, so as not to disturb the surface of the solution in the tube. (A centrifugal settler H-700R made by Kokusan Co. Ltd. was used.)

After centrifugal sedimentation, the supernatant liquid of the liquid contents centrifuged in the tube was slowly sucked up to a depth of about 1 cm above the lymphocyte layer centrifugally precipitated in the tube in an aseptical condition by using an aspirator so as not to suck in the lymphocyte cells. Then, the layer of the lymphocyte cells in the tube was sucked up by using a pipet of 5 ml in capacity so as not to suck in blood clots and collected with a 15 ml centrifugal settler tube of 15 ml in capacity, in which 10 ml of rinsing culture medium (RPMI1640+6) were contained in advance. Then, the centrifugal settler tube was covered with a lid and turned upside down several times to mingle. Thereafter, the centrifugal settler tube was centrifuged at 1800 rpm at a centrifugal separating temperature of 20° C. for 10 minutes.

After the centrifugal settler tube was further centrifuged, the supernatant liquid in the tube was removed, and cell sedimentum was thoroughly dispersed by using a vortex mixer. Finally, upon adding 10 ml of rinsing culture medium thereinto, the tube was turned upside down over again to mingle sufficiently the suspension. Then, the suspension in the tube was taken out by 500 $\mu$l to three 1.5 ml-microtubes (imported and sold by K.K. Asist) for measurement of the contents by percentage of CD3, HLA-DR and CD4 CD8 and analysis of the surface antigens of the cells to form three suspension samples.

6. Analysis of the Surface Antigens of the Cells:

The three suspension samples prepared in the process 5 above were centrifuged at 6000 rpm at a centrifugal separating temperature of 4° C. for 5 minutes to precipitate the cells by using a centrifugal settler (Model M-150 made by Sakuma Seisakujo, Inc.) Upon sucking up the supernatant liquid in each sample, 8 of $\mu$l PBS(−) and 8 $\mu$l of CD3/HLA-DR antibodies (Product No. 340048 imported and sold by Nippon Becton Dickinson Company, Ltd.) were added into a first sample tube, and 8 $\mu$l of CD4/CD8 antibodies (imported and sold by Nippon Becton Dickinson Company, Ltd.) were added into a second sample tube. Then, these samples were reacted for 30 minutes.

Into a third sample tube, 8 $\mu$l of PBS(−) were added for controlling the nonspecific reaction of the sample. After reaction, sheath fluid (ISOTON-2 made by Beckman Coulter, Inc.) was added into the respective samples tubes. Then, after stirring, the contents in the respective tubes were stirred by the vortex mixer and centrifuged at 6000 rpm at 4° C. for 5 minutes to precipitate the cells. Upon sucking out the supernatant liquid in each tube, 800 $\mu$l of sheath fluid were added. Then, the suspensions in the tubes were thoroughly stirred and transfused into FACS measuring tubes (imported and sold by Nippon Becton Dickinson Company, Ltd.), respectively.

The FACS measurement was performed by using a measuring device FACScan (imported and sold by Nippon Becton Dickinson Company, Ltd.) in accordance with an instruction manual attached to the device. The results thereof revealed that the contents by percentage of CD3, HLA-DR, CD4 and CD8 positive cells were 28%, 3%, 39% and 7% in the first sample, 18%, 1%, 17% and 3% in the second sample, and 15%, 4%, 16% and 8% in the third sample.

7. Measurement of the Number of Cells with Turk's Solution:

There was made a mixture of 10 $\mu$l of cells cultivated for seven days in the process 3 noted above and 40 $\mu$l of Turk's solution (made by Muto Kagaku Yakuhin).

The mixture thus obtained was applied by 10 $\mu$l to a hemocytometer (Product No. 9731 made by Perkin-Elmer Corporation) and measured to count the number of cells under a microscope (Model 211320 made by Olympus Optical Co., Ltd.) The measuring results revealed that the total numbers of the cells in the flasks were $1.7 \times 10^7$, $1.9 \times 10^7$ and $1.7 \times 10^7$, respectively.

8. Analysis of the Surface Antigens of the Cells on Seventh Day:

There was conducted an analysis of the surface antigens of the cells on FACS of the cells seven days after the cultivation starts in the aforementioned processes 3 and 4. The analyzing results revealed that the rates of CD3, HLA-DR, CD4 and CD8 were 98%, 10%, 79% and 20% in the first sample, 98%, 22%, 78% and 20% in the second sample, and 97%, 56%, 72% and 27 in the third sample.

Also, analyses of the CD45RA antibodies (Product No. 347723 imported and sold by Nippon Becton Dickinson Company, Ltd.) and CD45RO antibodies (Product No. 347967 imported and sold by Nippon Becton Dickinson Company, Ltd.) were conducted on their positivity seven days after the cultivation starts in the processes 3 and 4. The analyzing results revealed that the rates of the CD45RA and CD45RO were 7% and 73%, respectively. Since the activated lymphocytes derived from cord blood have practically positive CD45RO, they are considered to achieve superior antitumor effect and anti-infectious protective function.

Experimental Embodiment 2

Cultivation of Cord Blood Monocytes:

The cord blood monocytes isolated in the process 5 noted above were cultivated in the cultivating flask prepared in the process 1 noted above. As a result, the proliferation of the cells could be recognized.

Experimental Embodiment 3

Study in Promotion of Take of Hematogenous Stem Cells:

The cord blood-derived activated lymphocytes proliferated derived from a part of the cord blood transplanted to a patient who receives the cord blood in the manner as noted in the process 1 were administered to the patient. However, antibodies were not promptly yielded in the patient. It is evident from this fact that the activated lymphocytes derived from the cord blood have a function of promoting the take of hematogenous stem cells.

As is apparent from the foregoing description, the activated lymphocytes derived from cord blood and proliferated or the preparations containing the cord blood-derived activated lymphocytes according to the method of the present invention are excellently effective for preventing and treating various types of tumors and various types of infections. Besides, the cord blood-derived activated lymphocytes and the preparations thereof can be effectively used for not only preventing recurrence of the diseases noted above irrespective of whether or not transplantation is done, but also promoting the take of stem cells or other organs.

As can be readily appreciated, it is possible to deviate from the above embodiments of the present invention and, as will be readily understood by those skilled in this art, the invention is capable of many modifications and improvements within the scope and spirit thereof. Accordingly, it will be understood that the invention is not to be limited by these specific embodiments, but only by the scope and spirit of the appended claims.

What is claimed is:

1. Activated lymphocytes derived from cord blood, prepared by segregating lymphocytes from said cord blood and proliferating and activating said segregated lymphocytes directly in vitro.

2. The activated lymphocytes derived from the cord blood set forth in claim 1, wherein said lymphocytes derived from the cord blood are proliferated and activated with interleukin 2 and/or anti-CD3 antibody.

3. Activated lymphocytes derived from cord blood, prepared by segregating monocytes from cord blood and proliferating said segregated monocytes in vitro.

4. The activated lymphocytes derived from the cord blood set forth in claim 3, wherein said lymphocytes derived from the cord blood are proliferated and activated with interleukin 2 and/or anti-CD3 antibody.

5. Preparations for preventing or treating a tumor and an infection disease, containing activated lymphocytes derived from cord blood, said activated lymphocytes being prepared by segregating lymphocytes from said cord blood and proliferating and activating said segregated lymphocytes directly in vitro.

6. The preparations set forth in claim 5, wherein said lymphocytes derived from the cord blood are proliferated and activated with interleukin 2 and/or anti-CD3 antibody.

7. The preparations set forth in claim 5, wherein said infection disease is viral infection.

8. Preparations for preventing or treating a tumor and an infection disease, containing activated lymphocytes derived from cord blood, said activated lymphocytes being prepared by segregating monocytes from cord blood and proliferating said segregated monocytes in vitro.

9. The preparations set forth in claim 8, wherein said lymphocytes derived from the cord blood are proliferated and activated with interleukin 2 and/or anti-CD3 antibody.

10. Preparations for promoting take of stem cells of organs, containing activated lymphocytes derived from cord blood, said activated lymphocytes being prepared by segregating lymphocytes from said cord blood and proliferating and activating said segregated lymphocytes directly in vitro.

11. The preparations set forth in claim 10, wherein said lymphocytes derived from the cord blood are proliferated and activated with interleukin 2 and/or anti-CD3 antibody.

12. A kit for producing preparations for preventing or treating a tumor and an infection disease, said preparations containing activated lymphocytes derived from cord blood, said activated lymphocytes being prepared by segregating lymphocytes from said cord blood and proliferating and activating said segregated lymphocytes directly in vitro.

13. The kit set forth in claim 12, wherein said lymphocytes derived from the cord blood are proliferated and activated with interleukin 2 and/or anti-CD3 antibody.

14. A kit for producing preparations for preventing or treating a tumor and an infection disease, said preparations containing activated lymphocytes derived from cord blood, said activated lymphocytes being prepared by segregating monocytes from cord blood and proliferating said segregated monocytes in vitro.

15. The kit set forth in claim 14, wherein said lymphocytes derived from the cord blood are proliferated and activated with interleukin 2 and/or anti-CD3 antibody.

16. A method for producing preparations for preventing or treating a tumor and an infection disease, said preparations containing activated lymphocytes derived from cord blood, said activated lymphocytes being prepared by segregating lymphocytes from said cord blood and proliferating and activating said segregated lymphocytes directly in vitro.

17. The method set forth in claim 16, wherein said lymphocytes derived from the cord blood are proliferated and activated with interleukin 2 and/or anti-CD3 antibody.

18. A method for producing preparations for preventing or treating a tumor and an infection disease, said preparations containing activated lymphocytes derived from cord blood, said activated lymphocytes being prepared by segregating monocytes from cord blood and proliferating said segregated monocytes in vitro.

19. The method set forth in claim 18, wherein said lymphocytes derived from the cord blood are proliferated and activated with interleukin 2 and/or anti-CD3 antibody.

20. A method for preventing or treating a patient contracting a tumor or an infection disease, comprising deriving lymphocytes from cord blood, segregating said lymphocytes from said cord blood to obtain cord blood-derived lymphocytes, proliferating and activating said cord blood-derived lymphocytes directly in vitro to obtain activated cord blood-derived lymphocytes, and administering said activated cord blood-derived lymphocytes to the patient contracting the tumor or infection disease.

21. The method set forth in claim 20, wherein said lymphocytes derived from the cord blood are proliferated and activated with interleukin 2 and/or anti-CD3 antibody.

22. A method for preventing or treating a patient contracting a tumor or an infection disease, comprising deriving monocytes from cord blood, segregating said monocytes from said cord blood to obtain cord blood-derived lymphocytes, proliferating and activating said cord blood-derived lymphocytes directly in vitro to obtain activated cord blood-derived lymphocytes, and administering said activated cord blood-derived lymphocytes to the patient contracting the tumor or infection disease.

23. The method set forth in claim 22, wherein said lymphocytes derived from the cord blood are proliferated and activated with interleukin 2 and/or anti-CD3 antibody.

* * * * *